United States Patent
Reindl et al.

(12) 
(10) Patent No.: US 7,220,899 B1
(45) Date of Patent: May 22, 2007

(54) PLANTS HAVING ALTERED AMINO ACID CONTENTS AND METHOD FOR THE PRODUCTION THEREOF

(75) Inventors: Andreas Reindl, Mannheim (DE); Peter Ludwig Geigenberger, Dossenheim (DE); Horst-Ekkerhard Neuhaus, Kaiserslautern (DE); Karlheinz Graeve-Kampfenkel, Mainz-Kostheim (DE); Torsten Möhlmann, Bünde (DE); Joachim Tjaden, Kaiserslautern (DE)

(73) Assignee: BASF Plant Science GmbH (DE)

( * ) Notice: Subject to any disclaimer, the term of this patent is extended or adjusted under 35 U.S.C. 154(b) by 267 days.

(21) Appl. No.: 10/088,025

(22) PCT Filed: Aug. 5, 2000

(86) PCT No.: PCT/EP00/07625

§ 371 (c)(1),
(2), (4) Date: Mar. 14, 2002

(87) PCT Pub. No.: WO01/20009

PCT Pub. Date: Mar. 22, 2001

(30) Foreign Application Priority Data

Sep. 15, 1999 (DE) ................................ 199 44 212

(51) Int. Cl.
*C12N 15/63* (2006.01)
*C12N 15/82* (2006.01)
(52) U.S. Cl. .................... 800/320.1; 800/287; 800/298; 800/317.2
(58) Field of Classification Search ................ 800/278, 800/284, 285, 286, 287, 288, 298, 317.2, 800/320.1; 536/23.1, 23.2, 23.6, 24.1; 435/320.1, 435/183, 419, 465
See application file for complete search history.

(56) References Cited

U.S. PATENT DOCUMENTS 6,891,088 B1 * 5/2005 Neuhaus et al. ......... 800/317.2

FOREIGN PATENT DOCUMENTS

| WO | WO 94/10320 | * 5/1994 |
| WO | WO 99/58654 | 11/1999 |

OTHER PUBLICATIONS

Tjaden J. et al. The Plant Journal, 1998, vol. 16, No. 5; pp. 531-540.*
Tjaden Joachim et al: "Altered plastidic ATP/ADP-transporter activity influences potato (*Solanum tuberosum* L.) tuber morphology, yield and composition of tuber starch." Plant Journal, Bd. 16, Nr. 5, Dec. 1998, pp. 531-540.
Kampfenkel Karlheinz et al: "Molecular characterization of an *Arabidopsis thaliana* cDNA encoding a novel putative adenylate translocator of higher plants." FEBS Letters, Bd. 374, Nr. 3, 1995, pp. 351-355.
Database EMBL, Accession No. Z49227, Nov. 3, 1995, Kampfenkel, K.K.: "*A thaliana* mRNA for adenine nucleotide translocase".

* cited by examiner

*Primary Examiner*—Russell P. Kallis
(74) *Attorney, Agent, or Firm*—Connolly Bove Lodge & Hutz LLP (57) ABSTRACT

The invention relates to transformed plants and their descendants, which have altered regulative sequences and/or number of gene copies of the ATP/ADP-translocator-gene in such a manner that they have one or more amino acids simultaneously in altered amounts in comparison with a non-transformed plants. The invention also relates to a method for the production of said plants in addition to their use as crop plants or in the animal feedstuffs industry.

8 Claims, 4 Drawing Sheets

Fig. 1: Arabidopsis thaliana cDNA corresponding to the coding region of the chloroplast ATP/ADP translocator 1 (EMBL Accession Number Z49227)

atggaagctgtgattcaaaccagagggcttctctctttacccaccaaacccatcggagtgagaagcca
acttcagccttcccatggcttaaagcagagacttttcgccgcgaagccaagaaatctacatgggtgtct
ctatcctttaacgggcacaagaaatttcaaacctttgagccaaccctgcatgggatttcgatttcccaca
aagagagaagcaccgagttcatatgcaaggcggaggcgcggctgctggcgacggagctgtcttcg
gcgaagcgattccgcagctgttgtagcctcgcggaagattttcggtgtggaggttgcaaccttgaaaaa
gattatccctttaggattgatgttcttttgtattcttttcaattacacaattctgagggatacaaaggatgtcttg
gtggtgacggcgaaaggaagttctgctgagattatacctttcttgaagacttgggtgaatcttcctatggc
cattgggtttatgctcctctacactaaactctccaatgttctctccaagaaggctctgttttacactgttattgtc
cctttcatcatctactttgggggctttggtttcgtcatgtaccctctcagcaactatattcacccggaagctct
cgcagataagctccttacaaccctcggcccaagattcatgggtcctattgcaatattgcggatttggagtt
tctgtttgttttatgttatggctgagctttggggtagtgtggtggtctcagttctcttctggggctttgctaatcag
atcacaactgtggatgaagccaagaaattctatcctttgttcggcattggagccaatgttgcactgattttc
tcaggaagaaccgtgaaatacttctctaacttgagaaagaatcttggtcctggagttgacggcagtttcg
ttgaaagccatgatgagcattgtggtgggaatgggactcgcatttgtctctctattggtgggtcgaataga
tatgttcctcttccaacccgtagcaagaacaagaaggagaaaccgaagatgggaacgatggaaag
cttgaagttcttggtatcatcaccatacattagagatcttgctactttagtggtggcatacggtattagtatca
atcttgtggaagtcacatggaaatcaaagcttaaagctcagttccctagcccgaatgagtactcagcatt
tatgggagcattctcaacctgcacgggtgttgcaacattcacaatgatgcttctcagccaatacgtattca
ataagtatggttggggagtagctgcaaagatcaccccaactgttctgctattgactggtgttgcgttcttct
ctctaatattgtttggcggcccattcgcaccacttgttgccaagcttggtatgacaccgctacttgcagctgt
gtatgtcggtgcccttcagaatatcttcagcaagagtgccaagtacagcttgttcgacccttgcaaagaa
atggcctatatcccattggatgaggacaccaaggttaaaggcaaagctgcgattgacgtggtctgcaa
cccattaggaaaatcagggggagctttaatacagcagttcatgatcttatcctttggatcactagcgaatt
caacgccgtatctaggaatgatcttgttggttattgtcactgcgtggttagctgcagctaagtcgctggag
ggacagttcaacagcttgcgtctgaagaagagcttgagaaggaaatggagagagcttcatcggtga Fig. 2: Solanum tuberosum cDNA corresponding to the coding region of the chloroplast ATP/ADP translocator 1 (EMBL Accession Number Y10821)

atggaaggtgttttacaaacaagagggcttctttctttgccttctaaacccaaaatcaaggcttttacccat
tgcctcaaggggggtctaaggaacagattcaattctttaagtagtttaaagcctaatcctcttaatggggttt
ctttatcttcaaatgggtttcaaaaagttcaaggctttgacacaaagcctcagttgtttggccaaaagaag
aggtgttttccaatatgcaaagctgaggctgctgctgctgctggtgcagctgatggacagccacttttgtt
gaaaaggagcaacctaagtttatggggattgaacttgtgacccttaagaaaattataccacttggggcg
atgttcttttgtattctgtttaattatacaatccttagggatactaaggatgtgttggttgtaacagctaaggg
tccagtgctgagattatccctttcttgaaaacttgggtgaatttgcctatggctattggattcatgcttttgtac
acaaagttggctaatgtgttgtcaaaggaggctcttttttatactgttatacttccttttattgcattctttggggc
gtttggttttgttttgtatcctcttagcaattactttcaccctacagcttttgctgataagcttctcaataccttgg
tccaagatttcttggaccaattgctattctgaggatctggagtttctgcttgttctatgtcatggctgagctttg
gggaagtgtggtggtttcagtactcttttggggatttgctaatcagatcacgactgtcgatgaggctaaga
gattctatcctttgtttggacttggagcgaatgttgctcttatttctctggtcgcacagtgaagtacttttctag
cttgagaagctctttaggtcctggagttgatggttgggctatctccctgaaaggaatgatgagtattgttgt
gatgatgggtggggcaatctgtttcttttactggtgggtgaatagaaatgttgctctcccaactcgtagcaa
gaagaagaaggtaaaacctaacatgaccacaatggagagcttgaagttcttggtctcttcaaaatatat
cagggatcttgccacattggttgtagcatatggcattagtatcaaccttgttgaagttacatggaagtcaa
agctcaaagctcagttcccaagccccaatgaatactcctcattcatgggtgacttctcaactgctactgg
aatagcaactttcacaatgatgttgttaagtcaatggattttcgacaagtatgggtggggagcagcagcc
aagataacacctacagtcttgctccttaccggagttggtttcttctccctgcttttgtttgggggcacctctagc
acctactcttgcgaagtttggaatgactcctcttctagcagctgtctatgtgggtgcaatgcagaacattttc
agtaagagtgcaaagtatagtttgtttgaccctgcaaagaaatggcctacattcctttggatgaggaca
ccaaggttaaagggaaggcagcaatcgatgttgtctgcaatccactgggaaagtctggaggagctttg
atacaacagttcatgattttgacttttggttcacttgccagctcgacaccctaccttggcggtgtgctcttagt
aattgttcttgcatggttgggagcagccaagtctttggatggacagttcactcaattacgccaagaagaa
gatcttgagaaggaaatggagagagcatcgttgaagatccctgtcgtgtctcaaaatgaaaatggaa
atggtcctctctcaagtgagtcatcactaaatcccgctggaggtgactctaccaacgcttcatcggaacc
ctcctccccaaggagcctgtaa

Fig. 3: Plant transformation vector pBIN-AR-AATP1 for expressing the ATP/ADP translocator in sense orientation CaMV 35S:      cauliflower mosaic virus 35S promoter
AATP1 (A.t.):  EcoRV/BamHI fragment of the Arabidopsis thaliana ATP/ADP translocator 1 in sense orientation
OCS:           polyadenylation signal of the Agrobacterium tumefaciens octopine synthase gene Those restriction sites which cut the vector only once are also shown.

Fig. 4: Plant transformation vector pBIN-AR-AATP1-AS for expressing the ATP/ADP translocator in antisense orientation CaMV 35S: cauliflower mosaic virus 35S promoter
1PTAA (S.t.): BamHI/NdeI fragment of the Solanum tuberosum ATP/ADP translocator gene in antisense orientation
OCS: polyadenylation signal of the Agrobacterium tumefaciens octopine synthase gene Those restriction sites which cut the vector only once are also shown.

SEQUENCE LISTING

```
<160> NUMBER OF SEQ ID NOS: 2

<210> SEQ ID NO 1
<211> LENGTH: 1770
<212> TYPE: DNA
<213> ORGANISM: Arabidopsis thaliana

<400> SEQUENCE: 1
atggaagctg tgattcaaac cagagggctt ctctctttac ccaccaaacc catcggagtg      60
agaagccaac ttcagccttc ccatggctta aagcagagac ttttcgccgc gaagccaaga     120
aatctacatg ggtgtctcta tcctttaacg ggcacaagaa atttcaaacc tttgagccaa     180
ccctgcatgg gatttcgatt tcccacaaag agagaagcac cgagttcata tgcaaggcgg     240
aggcgcggct gctggcgacg gagctgtctt cggcgaagcg attccgcagc tgttgtagcc     300
tcgcggaaga ttttcggtgt ggaggttgca accttgaaaa agattatccc tttaggattg     360
atgttctttt gtattctttt caattacaca attctgaggg atacaaagga tgtcttggtg     420
gtgacggcga aaggaagttc tgctgagatt ataccttttct tgaagacttg ggtgaatctt     480
cctatggcca ttgggtttat gctcctctac actaaactct ccaatgttct ctccaagaag     540
gctctgtttt acactgttat tgtccctttc atcatctact ttgggggctt tggtttcgtc     600
atgtaccctc tcagcaacta tattcacccg gaagctctcg cagataagct ccttacaacc     660
ctcggcccaa gattcatggg tcctattgca atattgcgga tttggagttt ctgtttgttt     720
tatgttatgg ctgagctttg gggtagtgtg gtggtctcag ttctcttctg ggctttgct      780 aatcagatca caactgtgga tgaagccaag aaattctatc ctttgttcgg cattggagcc     840
aatgttgcac tgattttctc aggaagaacc gtgaaatact tctctaactt gagaaagaat     900
cttggtcctg gagttgacgg cagtttcgtt gaaagccatg atgagcattg tggtgggaat     960
gggactcgca tttgtctctc tattggtggg tcgaatagat atgttcctct tccaacccgt    1020
agcaagaaca agaaggagaa accgaagatg ggaacgatgg aaagcttgaa gttcttggta    1080
tcatcaccat acattagaga tcttgctact ttagtggtgg catacggtat tagtatcaat    1140
```

-continued

```
cttgtggaag tcacatggaa atcaaagctt aaagctcagt tccctagccc gaatgagtac   1200
tcagcattta tgggagcatt ctcaacctgc acgggtgttg caacattcac aatgatgctt   1260
ctcagccaat acgtattcaa taagtatggt tggggagtag ctgcaaagat caccccaact   1320
gttctgctat tgactggtgt tgcgttcttc tctctaatat tgtttggcgg cccattcgca   1380
ccacttgttg ccaagcttgg tatgacaccg ctacttgcag ctgtgtatgt cggtgccctt   1440
cagaatatct tcagcaagag tgccaagtac agcttgttcg acccttgcaa agaaatggcc   1500
tatatcccat ggatgagga caccaaggtt aaaggcaaag ctgcgattga cgtggtctgc   1560
aacccattag gaaaatcagg gggagcttta atacagcagt tcatgatctt atcctttgga   1620
tcactagcga attcaacgcc gtatctagga atgatcttgt tggttattgt cactgcgtgg   1680
ttagctgcag ctaagtcgct ggagggacag ttcaacagct tgcgtctgaa gaagagcttg   1740
agaaggaaat ggagagagct tcatcggtga                                    1770
```

<210> SEQ ID NO 2
<211> LENGTH: 1896
<212> TYPE: DNA
<213> ORGANISM: Solanum tuberosum

<400> SEQUENCE: 2

```
atggaaggtg ttttacaaac aagagggctt ctttctttgc cttctaaacc caaaatcaag    60 gcttttacc cattgcctca aggggtcta aggaacagat tcaattcttt aagtagttta    120
aagcctaatc ctcttaatgg ggtttcttta tcttcaaatg ggtttcaaaa agttcaaggc   180
tttgacacaa agcctcagtt gtttggccaa agaagagggt gttttccaat atgcaaagct   240
gaggctgctc ctgctgctgg tgcagctgat ggacagccac tttttgttga aaaggagcaa   300 cctaagtttta tggggattga acttgtgacc cttaagaaaa ttataccact tggggcgatg   360 ttctttttgta ttctgtttaa ttatacaatc cttaggggata ctaaggatgt gttggttgta   420
acagctaaag ggtccagtgc tgagattatc cctttcttga aaacttgggt gaatttgcct   480
atggctattg gattcatgct tttgtacaca agttggctaa atgtgttgtc aaaggaggct   540
cttttttata ctgttatact tccttttatt gcattctttg gggcgtttgg ttttgttttg   600
tatcctctta gcaattactt tcaccctaca gcttttgctg ataagcttct caatacccct   660
ggtccaagat tcttggacc aattgctatt ctgaggatct ggagtttctg cttgttctat   720
gtcatggctg agctttgggg aagtgtggtg gtttcagtac tcttttgggg atttgctaat   780
cagatcacga ctgtcgatga ggctaagaga ttctatcctt tgtttggact tggagcgaat   840
gttgctctta ttttctctgg tcgcacagtg aagtactttt ctagcttgag aagctcttta   900
ggtcctggag ttgatggttg ggctatctcc ctgaaaggaa tgatgagtat tgttgtgatg   960
atgggtgggg caatctgttt cttttactgg tgggtgaata aaatgttgc tctcccaact  1020 cgtagcaaga agaagaaggt aaaacctaac atgaccacaa tggagagctt gaagttcttg  1080
gtctcttcaa atatatcag ggatcttgcc acattggttg tagcatatgg cattagtatc  1140
aaccttgttg aagttacatg gaagtcaaag ctcaaagctc agttcccaag ccccaatgaa  1200
tactcctcat tcatgggtga cttctcaact gctactggaa tagcaacttt cacaatgatg  1260
ttgttaagtc aatggatttt cgacaagtat gggtggggag cagcagccaa gataacacct  1320
acagtcttgc tccttaccgg agttggtttc ttctccctgc ttttgtttgg ggcacctcta  1380
gcacctactc ttgcgaagtt tggaatgact cctcttctag cagctgtcta tgtgggtgca  1440
```

-continued

| | | | | | |
|---|---|---|---|---|---|
| atgcagaaca | ttttcagtaa | gagtgcaaag | tatagtttgt | ttgacccctg | caaagaaatg | 1500
| gcctacattc | ctttggatga | ggacaccaag | gttaaaggga | aggcagcaat | cgatgttgtc | 1560
| tgcaatccac | tgggaaagtc | tggaggagct | ttgatacaac | agttcatgat | tttgactttt | 1620
| ggttcacttg | ccagctcgac | accctacctt | ggcggtgtgc | tcttagtaat | tgttcttgca | 1680
| tggttgggag | cagccaagtc | tttggatgga | cagttcactc | aattacgcca | agaagaagat | 1740
| cttgagaagg | aaatggagag | agcatcgttg | aagatccctg | tcgtgtctca | aaatgaaaat | 1800
| ggaaatggtc | ctctctcaag | tgagtcatca | ctaaatcccg | ctggaggtga | ctctaccaac | 1860
| gcttcatcgg | aaccctcctc | cccaaggagc | ctgtaa | | | 1896

PLANTS HAVING ALTERED AMINO ACID CONTENTS AND METHOD FOR THE PRODUCTION THEREOF

This application is the U.S. national phase of international application PCT/EP00/07625 filed Aug. 5, 2000 which designated the U.S.

The present invention relates to transformed plants and their progeny whose regulatory sequences and/or gene copy number of the ATP/ADP translocator gene are modified in such a way that they exhibit one or more amino acids simultaneously in modified amounts in comparison with an untransformed plant. The present invention furthermore relates to a method of generating these plants and to their use as useful plant or in sectors of the feedstuff industry.

Humans and animals are only capable of synthesizing 11 out of the 20 amino acids and therefore depend on taking up the 9 what are known as essential amino acids via the food. The nutrition of humans and livestock is predominantly based on plant components. The essential amino acids include lysine, tryptophan, valine, leucine, isoleucine, methionine, threonine, phenyl-alanine and histidine.

The fact that the concentration of these amino acids in food plants is frequently only very low gives rise to a problem. This is why grain mixtures and vegetable-based foodstuffs are frequently supplemented with synthetically produced amino acids in order to increase their nutritional value.

In the past, a number of avenues were followed to increase the amounts of free amino acids, i.e. amino acids which are not found in proteins. However, these attempts focused mainly on traditional breeding and on the selection of mutants.

In the recent past, there have been increasing attempts to increase the amounts of essential amino acids by applying molecular-genetic techniques. WO 97/28247, WO 98/13506 and WO 97/35023 describe first attempts at extending the heterologous expression of a seed-specific storage protein which is high in lysine or methionine. The disadvantage here is that the amino acids are stored in proteins, that is to say that, again, the increase takes the form of an increase in bound amino acids.

Furthermore, a large number of attempts for directly controlling amino acid biosynthesis are known. In these attempts, individual genes encoding specific amino acid biosynthesis enzymes were overexpressed in plants, resulting in an increase in the biosynthesis end products in question.

As an alternative, it has furthermore been attempted to control the reaction kinetics of enzymes. What is known as the product inhibition of enzymes causes a particular problem here. For example, Shaul and Galili (1993; Plant Mol Biol 23: 759-768) and Falco et al. (1995; Bio/Technology 13: 577-582) describe plants which overproduce free lysine, coupled with a decrease in free threonine. The enzyme responsible is aspartate kinase, the first enzyme in the biosynthesis of the amino acids derived from aspartate and which is inhibited allosterically by lysine. To circumvent this feedback inhibition, recombinantly modified aspartate kinase genes were overexpressed in plants (WO 94/25605). This modified aspartate kinase has a greatly reduced feedback inhibition by lysine and threonine, leading to an increase in lysine. This aspartate kinase which is insensitive to feedback inhibition by lysine was furthermore overexpressed together with other biosynthesis enzymes. Suitable experiments were carried out in Corynebacteria (1991, Applied and Environmental Microbiology 57: 1746-1752). In these bacteria, however, not only an increase in lysine results, but also a pronounced decrease in the growth rate, which, in turn, has a negative effect on the lysine balance.

Experiments with plants having both a feedback-insensitive aspartate kinase and a feedback-insensitive dihydropicolinate synthase are described by Shaul and Galili (1993; Plant Mol Biol 23: 759-768). These two enzymes have a key position in amino acid biosynthesis. However, overexpression of these bottleneck enzymes did not result in the hoped-for increase of the two amino acids lysine and threonine. Rather, only the free lysine content was increased, with the free threonine content simultaneously going down drastically.

Beyond the overexpression of one or two amino acid biosynthesis genes, WO 98/56935, EP 0 854 189 and EP 0 485 970 describe multi-gene approaches which aim at influencing the amounts of one or more amino acids simultaneously in one plant. A prerequisite therefor is the genetic modification of a plant with regard to several genes; i.e. it would be necessary to generate a multi-transgenic plant. However, these methods are very complicated. Moreover, such massive interference with hereditary material of the plant increasingly harbours risks of unpredictable side reactions.

It is an object of the present invention to provide transgenic plants and a method of generating them without the abovementioned disadvantages.

We have found that this object is surprisingly achieved in accordance with the invention by providing a transformed plant whose regulatory sequences and/or gene copy number of an ATP/ADP translocator gene are modified in such a way that it exhibits one or more amino acids simultaneously in modified amounts in comparison with a corresponding untransformed plant.

The transformed plants are distinguished in accordance with the invention by exhibiting predominantly one or more essential amino acid(s) in modified amounts.

In particular, the plants according to the invention exhibit one or more essential amino acid(s) whose content is increased over that of the untransformed plants.

The transformed plants are, in accordance with the invention, useful plants, preferably economically relevant plants, such as, for example, potatoes or maize. However, the present invention is not restricted to these genera.

The present invention relates both to the above-mentioned transformed plants, their seeds and progeny and also to tissue, cells or material capable of propagation derived from these transformed plants.

In one embodiment of the present invention in which the gene encoding the ATP/ADP translocator is overexpressed in accordance with the invention in potatoes, an increase in amino acids which are interesting from the nutritional and economical point of view, such as lysine, methionine, threonine, valine, tryptophan, histidine, isoleucine and leucine, is achieved.

In the transformed plant referred to as line 98, the amount of free lysine is increased by 28%; in the transgenic plant referred to as line 62, the increase in the amount of free lysine is 25.75%. Surprisingly, an at least 25% increase in the lysine content is achieved by increasing the ATP/ADP translocator activity in the plants by only 50%. Furthermore, the amount of methionine in line 98 is increased by 11%. In addition to increased amounts of lysine and methionine, increased amounts of the essential amino acids valine (12% in line 98), tryptophan (50% in line 98), threonine (12.5% in line 98), histidine (23.5% in line 98 and 20% in line 62), isoleucine (25% in line 98) and leucine (40% in line 98) are also found.

Accordingly, overexpression of the ATP/ADP translocator in antisense orientation results in a reduction of the amounts of amino acid in the respective transformed plants, referred to as lines 594 and 595. In the case of lysine, only approximately a quarter of the wild-type lysine quantity is found here; while in the case of methionine only approximately not more than one eighth of the wild-type methionine quantity is found.

An overview over the amino acid spectrum in the wild type of potato, Solanum tuberosum, and in transformed potato plants is compiled in Table 1. In this embodiment of the invention, the total amount of free amino acids in the transformed potato plants is increased by approximately 7% over the wild type.

A particular advantage of the present invention is that the increased expression of a single gene, viz. of the ATP/ADP translocator, can bring about a specific increase of several, predominantly essential, amino acids simultaneously.

In accordance with the invention, the transformed plant is distinguished by the fact that it has an increased transport capacity for ATP into the chloroplast membrane.

The invention furthermore relates to an ATP/ADP translocator gene for use in one of the above-described plants with an *Arabidopsis thaliana* amino acid sequence (EMBL Accession No. Z49227) encoding by the nucleotide sequence shown in FIG. 1 (SEQ ID NO:1).

In accordance with the invention, the use of any ATP/ADP translocator gene from organisms which have chloroplasts is feasible. Preferred organisms are plants in general, green algae or mosses.

Normally, the ATP/ADP translocator gene is localized in the internal chloroplast membrane, where it is responsible for the antiport, i.e. the opposite transport, of ATP and ADP, by exporting chloroplast ADP into the cytosol in exchange for ATP. Owing to the increased activity of this ATP/ADP translocator, the amount of ATP in the chloroplast is increased (Neuhaus et al., 1997, The Plant Journal 11: 73-82). Tjaden et al. (1998, Plant Journal 16: 531-540) demonstrated that the uptake of ATP into potato chloroplasts owing to overexpression of the ATP/ADP translocator out performs the uptake capacity of the wild type by an average of 50%. These energy-rich ATP molecules, which are now increasingly available, can be exploited for the increased biosynthesis of starch and fatty acids as described by Möhlmann et al., 1994, Planta, 194: 492-497; Neuhaus et al., 1993, Plant Physiology 101: 573-578; Tjaden et al., 1998, Plant Journal 16: 531-540.

In accordance with the invention, an ATP/ADP translocator gene with a naturally, chemically synthesized, modified, artificially generated nucleotide sequence with essentially the same action or with heterologous nucleotide sequences encoding an ATP/ADP translocator or allelic variations or isoforms thereof or with mixtures thereof may also be employed.

Sequences which encode an ATP/ADP translocator gene with essentially the same action are those sequences which, despite a deviating nucleotide sequence, retain the desired functions. Equivalents with the same action thus encompass naturally occurring variants of the described sequences, but also artificial nucleotide sequences, for example those obtained by chemical synthesis, which are adapted to the codon usage of a plant.

A nucleotide sequence with the same action is also understood as meaning, in particular, natural or artificial mutations of an originally isolated sequence encoding an ATP/ADP translocator and retaining the desired function. Mutations encompass substitutions, additions, deletions, exchanges or insertions of one or more nucleotide residues. Thus, for example, the present invention also extends to those nucleotide sequences which are obtained by modifying the ATP/ADP translocator nucleotide sequence. The purpose of such a modification may be, for example, the further delimitation of the coding sequence contained therein, or else, for example, the insertion of further cleavage sites for restriction enzymes.

Nucleotide sequences with the same action are also those variants whose function is reduced or increased compared with the original gene or gene fragment.

Suitable DNA sequences are, furthermore, artificial DNA sequences as long as they confer the desired properties, as described above. Such artificial DNA sequences can be determined for example by back-translating proteins constructed by means of molecular modelling which have an ATP/ADP translocator activity, or else by in-vitro selection. Especially suitable are coding DNA sequences which have been obtained by back-translating a polypeptide sequence in accordance with the host-plant-specific codon usage. The specific codon usage can be determined readily by a skilled worker familiar with plant genetic methods by means of computer evaluations of other, known genes of the plant to be transformed.

The invention furthermore encompasses an ATP/ADP translocator gene which is operably linked to regulatory nucleotide sequences. The regulatory sequences also include, inter alia, an upstream promoter which makes possible expression in plants.

Operable linkage is understood as meaning the sequential arrangement of, for example, promoter, coding sequence, terminator and, if appropriate, further regulatory elements in such a way that each of the regulatory elements can fulfil its intended function upon expression of the coding sequence. Suitable as promoter is, in principle, any promoter capable of governing the expression of foreign genes in plants. A plant promoter or a promoter derived from a plant virus is preferably used. Particularly preferred is the cauliflower mosaic virus CaMV 35S promoter (Franck et al., Cell 21 (1980), 285-294). As is known, this promoter contains various recognition sequences for transcriptional effectors which, in their totality, bring about permanent and constitutive expression of the gene introduced (Benfey et al., EMBO J, 8 (1989), 2195-2202).

Further sequences which are preferred for operable linkage, but not limited thereto, are transcription terminators and translation enhancers, such as the tobacco mosaic virus 5' leader sequence (Gallie et al., Nucl. Acids Res. 15 (1987), 8693-8711).

Adaptors or linkers can be attached to the fragments to connect the DNA fragments with each other. Preferably, the promoter and the terminator regions can be provided, in the direction of transcription, with a linker or polylinker comprising one or more restriction sites for insertion of this sequence. As a rule, the linker has 1 to 10, preferably 1 to 8, especially preferably 2 to 6, restriction sites. In general, the linker has a size of less than 100 bp within the regulatory regions, frequently less than 60 bp, but at least 5 bp. The promoter can be native, or homologous, or else foreign, or heterologous, relative to the host plant.

The invention furthermore relates to a gene structure comprising an ATP/ADP translocator gene and regulatory sequences linked operably to this gene and a vector comprising an ATP/ADP translocator gene or a gene structure as described above. In this context, the vector may comprise additional regulatory nucleotide sequences, preferably from the group of the promoters, terminators or translation enhancers, and nucleotide sequences for the replication in a suitable host cell or for integration into its genome.

Using recombination and cloning techniques known per se, the gene structures can be cloned into suitable vectors which make possible their amplification in host cells such as, for example, plants, plant tissues or plant cells. Suitable vectors are described, inter alia, in "Methods in Plant Molecular Biology and Biotechnology" (CRC Press), Chapter 6/7, pp. 71-119 (1993).

Suitable as cloning vectors for *E. coli* as host cell are, in particular, pBR332, pUC series, M13mp series and pACYC1 84. Especially preferred are binary vectors which are capable of replication both in *E. coli* and in, for example, agrobacteria. An example of a binary vector which may be mentioned is pBIN19 (Bevan et al., Nucl. Acids Res. 12 (1984), 8711). For example, the gene structure according to the invention may also be incorporated into tobacco transformation vector pBIN-AR-TP.

The present invention furthermore relates to a method of generating an above-described transformed plant, wherein an ATP/ADP translocator gene, a gene structure or a vector of the above-described type is transferred into the plant or tissue or cells thereof by recombinant methods. In general, the transfer of DNA is to be understood as meaning the transformation of plants, plant tissue or plant cells.

Suitable methods for the transformation and regeneration of plants from plant tissues or plant cells for transient or stable transformation are protoplast transformation by polyethylene glycol-induced DNA uptake, the biolistic method with the gene gun—what is known as the particle bombardment method-, electroporation, the incubation of dry embryos in DNA-containing solution, microinjection and the agrobacterium-mediated gene transfer. The methods mentioned are described, for example, in B. Jenes et al., Techniques for Gene Transfer, in: Transgenic Plants, Vol. 1, Engineering and Utilization, edited by S. D. Kung and R. Wu, Academic Press (1993), 128143 and in Potrykus, Annu. Rev. Plant Physiol. Plant Molec. Biol. 42 (1991), 205225).

The present invention thus makes possible the generation of economically valuable useful plants which are distinguished by a substantially increased amino acid content, in particular a substantially increased essential amino acid content.

The present invention furthermore relates to the use of the transformed plant as useful plant or fodder plant. Since the content of several essential amino acids may be increased in the useful plants according to the invention, in particular simultaneously, expensive supplementation of the feedstuffs with amino acids which previously had to be produced or obtained separately by conventional methods and externally admixed to the feed can advantageously be dispensed with.

The transformed plant in accordance with the invention, its seed and its progeny, and tissue or cells thereof or extracts thereof, can furthermore be used in sectors of agriculture, the feedstuff industry, the pharmaceutical industry or in the health sector.

In the following text, the present invention is illustrated in greater detail by use examples which, however, do not limit the scope of the invention:

BRIEF DESCRIPTION OF THE FIGURES

FIG. 1 shows *Arabidopsis thaliana* cDNA corresponding to the coding region of the chloroplast ATP/ADP translocator 1 (EMBL Accession Number Z49227) (SEQ ID NO:1).

FIG. 2 shows *Solanum tuberosum* cDNA corresponding to the coding region of the chloroplast ATP/ADP translocator 1 (EMBL Accession Number Y10821) (SEQ ID NO:2).

1. General Cloning Methods

Cloning methods such as, for example, restriction cleavages, agarose gel electrophoresis, purification of DNA fragments, transfer of nucleic acids to nitro-cellulose and nylon membranes, linking DNA fragments, transformation of *E. coli* cells, bacterial cultures, phage multiplication, and sequence analysis of recombinant DNA, were carried out as described by Sambrook et al. (1989, Cold Spring Harbor Laboratory Press: ISBN 0-87969-309-6).

The bacterial strains used (*E. coli*, XL-I Blue) were obtained from Stratagene (Heidelberg) or Qiagen (Hilden). The agrobacterial strain used for the transformation of the plants (*Agrobacterium tumefaciens*, C58C1 with the plasmid pGV2260 or pGV3850kan) was described by Deblaere et al. in Nucl. Acids Res. 13 (1985), 4777. As an alternative, the agrobacterium strain LBA4404 (Clontech) or other suitable strains may also be employed.

The vectors pUC19 (Yanish-Perron, Gene 33 (1985), 103-119) pBluescript SK-(Stratagene), pGEM-T (Promega), pZerO (Invitrogen) pBin19 (Bevan et al., Nucl. Acids Res. 12 (1984), 8711-8720) and pBinAR (Höfgen and Willmitzer, Plant Science 66 (1990), 221-230) may be used for cloning.

2. Transformation of Agrobacteria

*Agrobacterium tumefaciens* was transformed following the method of Höfgen and Willmitzer (Nucl. Acid Res. (1988) 16, 9877). The agrobacteria were grown in YEB medium (Vervliet et al., J. Gen. Virol. (1975) 26, 33).

3. Sequence Analysis of Recombinant DNA

Recombinant DNA molecules were sequenced using a Licor laser fluorescence DNA sequencer (sold by MWG Biotech., Ebersbach) following the method of Sanger (Sanger et al., Proc. Natl. Acad. Sci. USA 74 (1977), 5463-5467).

4. Construction of a Plant Transformation Vector with AATP1 in Sense Orientation To construct a vector for transforming plants, a 2230 bp EcoRV/BamHI fragment of the *Arabidopsis thaliana* AATP1 cDNA (the cloning of AATP1 from *Arabidopsis thaliana* is described in Kampfenkel et al., FEBS Letters 374 (1995), 351-355 and Neuhaus et al., The Plant Journal 11: 73-82) is ligated into an SmaI/EcoRV- and BamHI-cut vector pBinAR (Höfgen and Willmitzer, Plant Science 66 (1990), 223-230). Insertion of the cDNA fragment gives rise to a gene construct comprising the cauliflower mosaic virus 35S promoter (540 bp) and the protein-encoding region of the *Arabidopsis thaliana* ADP/ATP translocator 1 (AATP1). The cDNA fragment is fused in sense orientation to the 35S promoter in pBinAR. The polyadenylation signal of the *Agrobacterium tumefaciens* octopine synthase gene (215 bp) follows in the 3' direction of the inserted AATP1 fragment.

Figure 3:
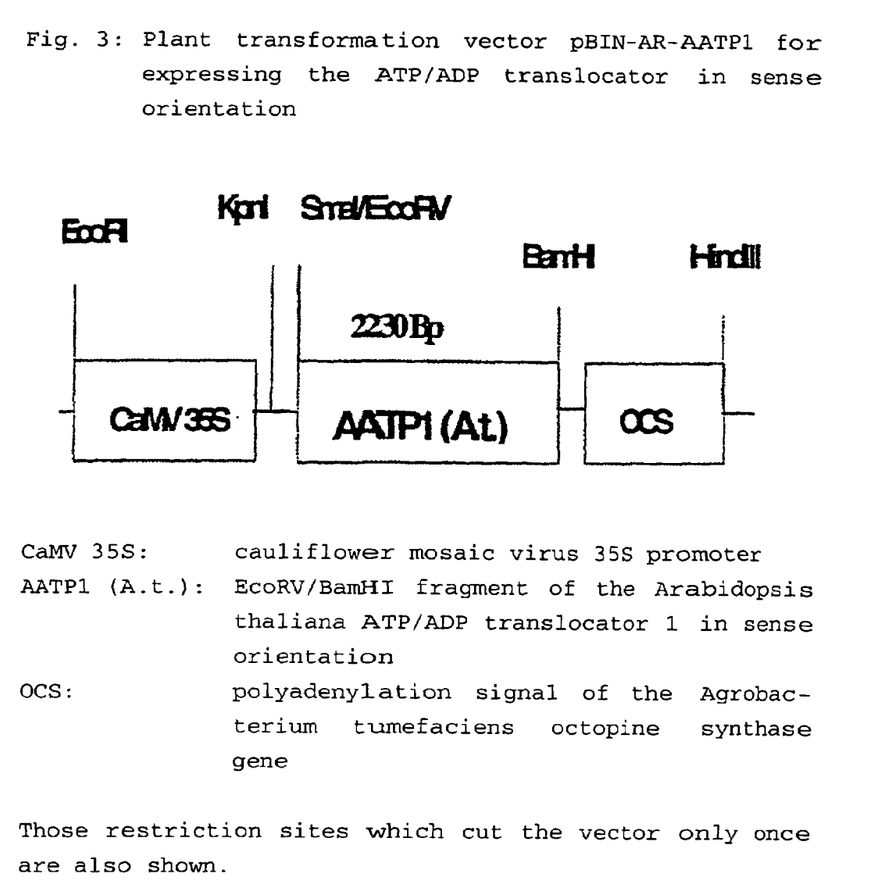
FIG. 3 shows the plant transformation vector pBIN-AR-AATPI for expressing the ATP/ADP translocator in sense orientation.

The overall size of the plasmid pBIN AR-AATP1 (FIG. 3) is approx. 14.2 kb.

5. Insertion of the Plasmid pBINAR-ATTP1 into the Genome of Potato Plants

The plasmid is transferred into potato plants with the aid of *Agrobacterium tumefaciens* as described by Rocha-Sosa et al. (EMBO J. 8 (1989), 23-29). Transgenic potato plants with an increased level of the plastid ADP/ATP translocator 1 mRNA acted as positive control for the transformation. Detection is by Northern blot analysis. To this end, RNA is isolated from potato leaf and tuber tissue following standard protocols. 50 µg of RNA are separated on an agarose gel (1.5% agarose, 1×MEN buffer, 16.6% formaldehyde). Following electrophoresis, the RNA is transferred to a Hybond N nylon membrane (Amersham, UK) by capillary blotting, using 20×SSC. The RNA is immobilized on the membrane by UV irradiation, and the membrane is prehybridized for 2 hours in phosphate hybridization buffer (Sambook et al., 1989, Cold Spring Harbor Laboratory Press: ISBN 0-87969-309-6) and subsequently hybridized for 10 hours by adding the radiolabelled probe.

6. Construction of a Plant Transformation Vector with AATP1 in Antisense Orientation To construct a vector for the transformation of plants, a 1 265 bp BamHI/NdeI fragment in which the NdeI cleavage site is made blunt-ended with T4 polymerase is ligated from the coding region of the *S. tuberosum* AATP1 cDNA (description of the potato AATP1 cloning in Tjaden et al., 1998, The Plant Journal 16: 531-540) into an SmaI- and BamHI-cut vector pBinAR (Höfgen and Willmitzer, Plant Science 66 (1990), 221-230). The NdeI cleavage site is located in the AATP1 cDNA, and the BamHI cleavage site is derived from vector pTM1 (Tjaden et al., 1998, The Plant Journal 16: 531-540). Insertion of the cDNA fragment gives rise to a gene construct comprising the cauliflower mosaic virus 35S promoter (540 bp) and a 1 265 bp region of an ADP/ATP translocator 1 from *S. tuberosum* (AATP1 S.t.) in antisense orientation. The fragment was fused with the 35S promoter in pBinAR. The polyadenylation signal of the *Agrobacterium tumefaciens* octopine synthase gene (215 bp) follows in the 3' direction of the inserted AATP1 fragment.

Figure 4:
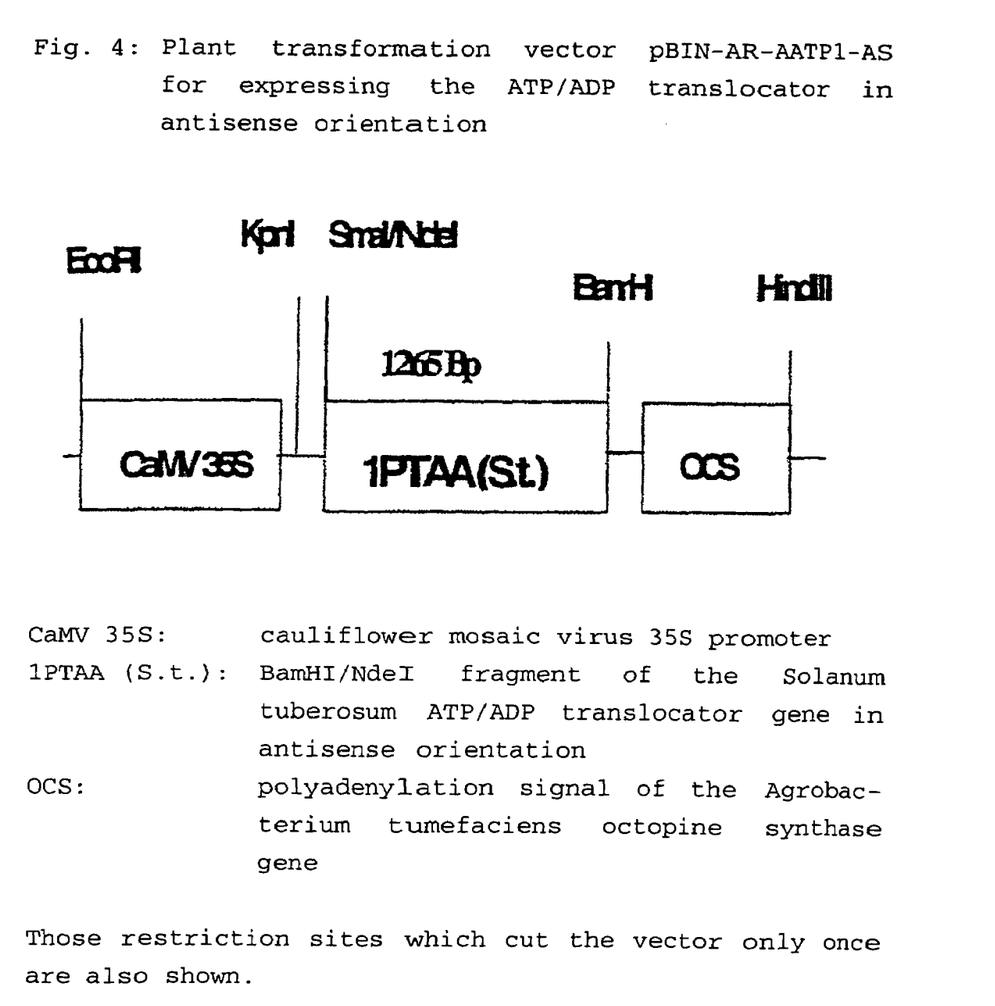
FIG. 4 shows the plant transformation vector pBIN-AR-AATPI-AS for expressing the ATP/ADP translocator in antisense orientation.

The overall size of the plasmid pBIN AR-AS-AATP1 (FIG. 4) is approx. 13.3 kb.

7. Introduction of the Plasmid pBINAR-ASAATP1 into the Genome of Potato Plants

The plasmid is transferred similarly to the procedure described under item 5.

As the result of the transformation, transgenic potato plants showed a reduced level of the mRNA of a plastid ADP/ATP translocator. This is detected by Northern blot analysis. To this end, RNA is isolated from potato leaf and tuber tissue following standard protocols. 50 µg of RNA were separated on an agarose gel (1.5% agarose, 1×MEN buffer, 16.6% formaldehyde). Following electrophoresis, the RNA was transferred to a Hybond N nylon membrane (Amersham, UK) by capillary blotting, using 20×SSC. The RNA is immobilized on the membrane by UV irradiation. The membrane is prehybridized for 2 hours in phosphate hybridization buffer (Sambrook et al., loc. cit.) and subsequently hybridized for 10 hours by adding the radiolabelled probe.

8. Amino Acid Analysis

The amine acids (with the exception of proline) were measured in ethanolic extracts following HPLC separation (method of Geigenberger et al., 1996, Plant Cell & Environ. 19: 43-55).

8.1 Preparation of the Ethanolic Extract

In each case two potato discs (total fresh weight approx. 0.2 g) are extracted for 30 minutes at 80° C. in two successive steps using in each case 7 ml of 80% (v/v) ethanol and 7 ml of 50% ethanol. The total extract (approximate volume 14 ml) is used for the amino acid analysis.

8.2 Determination of the Amino Acid Contents by HPLC

The amino acids were detected fluorometrically following pre-column derivatization of the primary amino group with o-phthaldialdehyde (OPA). To this end, an injector (Autosampler 465, Kontron, Eching) injects 35 µl of OPA reagent composed of a mixture of 5% (w/v) OPA in methanol, 0.8 M borate buffer (pH 10.4 with KOH) and 3-mercaptopropionic acid (10:90:1, v:v:v) at 4° C. into 35 µl of extract. After 108 seconds, 20 µl of the derivatized sample were injected.

Mobile phase A is a mixture of 1 000 ml of 12 mM sodium phosphate (pH 6.8) and 1.6 ml of tetrahydrofuran. Mobile phase B is composed of a mixture of 250 ml of 12 mM sodium phosphate (pH 6.8), 175 ml of methanol and 110 ml of acetonitrile. The separation conditions are as follows: minute 0-2, isocratic phase with 0% B, minute 2-11, linear gradient from 0 to 10% B, minute 11-17, 10% B, minute 17-27, linear gradient from 10 to 50% B, minute 27-38, linear gradient from 50 to 60% B, minute 38-44, linear gradient from 60 to 100% B, minute 44-46, 100% B, minute 46-48, 100% to 0% B, minute 48-60, 0% B. A Hypersil ODS column (particle size 3 µm, length 150 mm, diameter 4.6 mm, Knauer GmbH, Berlin) is used for the separation. The signals detected by the fluorimeter (SFM25, Kontron, Eching) (excitation wavelength=330 nm, emission wavelength=450 nm) are integrated and evaluated by the data processing system 450-MT (Kontron, Eching).

8.3 Determination of the Proline Content

The proline content is determined by the method of Bates et al., 1973, Plant Soil 39: 205-207. 500 µl of a mixture of 2 parts of 6 M $H_3PO_4$ and 3 parts of 75% acetic acid and 500 µl of ninhydrin solution (600 mg per 20 ml of 75% acetic acid) are added to 200 µl of extract. After incubation for 45 minutes at 95-100° C., the text mixture is placed on ice and mixed with 300 µl of toluene. Following phase separation, the top phase is transferred into a microcuvette, and the OD is measured at 515 nm. The proline content is determined by comparison with a calibrating plot (1-50 µM proline).

TABLE 1

Overview of the amino acid content in the *Solanum tuberosum* wild type and in the transformed potato plants comprising the ATP/ADP translocator gene in sense orientation (Sense-98 and Sense-62) or in antisense orientation (Antis-594 and Antis-595).

| Genotype | Aspartate | Glutamate | Aspartic acid | Serine | Glutamine |
|---|---|---|---|---|---|
| Wild type | 2.020 | 2.090 | 11.190 | 1.066 | 5.586 |
| Sense-98 | 1.656 | 2.238 | 8.986 | 1.008 | 7.409 |
| Sense-62 | 1.924 | 1.540 | 12.533 | 0.838 | 6.949 |
| Antis-594 | 0.746 | 4.123 | 1.256 | 0.875 | 5.633 |
| Antis-595 | 0.880 | 4.670 | 4.344 | 1.057 | 6.931 |

| Genotype | Tyrosine | Valine | Methionine | Tryptophan | Phenylalanine |
|---|---|---|---|---|---|
| Wild type | 1.201 | 3.589 | 0.986 | 0.519 | 1.544 |
| Sense-98 | 1.840 | 4.010 | 1.098 | 0.780 | 2.286 |
| Sense-62 | 1.440 | 3.633 | 0.920 | 0.506 | 1.620 |
| Antis-594 | 0.474 | 2.620 | 0.403 | 0.143 | 2.039 |

TABLE 1-continued

Overview of the amino acid content in the *Solanum tuberosum* wild type and in the transformed potato plants comprising the ATP/ADP translocator gene in sense orientation (Sense-98 and Sense-62) or in antisense orientation (Antis-594 and Antis-595).

| Antis-595 | 0.228 | 2.340 | 0.510 | 0.019 | 1.716 |

| Genotype | Glycine | Threonine | Histidine | Alanine | Arginine |
| --- | --- | --- | --- | --- | --- |
| Wild type | 0.473 | 1.168 | 0.699 | 1.036 | 1.809 |
| Sense-98 | 0.507 | 1.318 | 0.865 | 1.694 | 2.122 |
| Sense-62 | 0.442 | 1.197 | 0.838 | 1.165 | 2.008 |
| Antis-594 | 0.448 | 0.612 | 0.265 | 1.824 | 0.493 |
| Antis-595 | 0.641 | 0.574 | 0.292 | 1.562 | 0.396 |

TABLE 1-continued

Overview of the amino acid content in the *Solanum tuberosum* wild type and in the transformed potato plants comprising the ATP/ADP translocator gene in sense orientation (Sense-98 and Sense-62) or in antisense orientation (Antis-594 and Antis-595).

| Genotype | Isoleucine | Leucine | Lysine | Proline | Free ASs, total |
| --- | --- | --- | --- | --- | --- |
| Wild type | 1.450 | 0.212 | 1.027 | 0.595 | 41.7 |
| Sense-98 | 1.819 | 0.296 | 1.310 | 0.552 | 44.7 |
| Sense-62 | 1.445 | 0.195 | 1.291 | 0.546 | 43.9 |
| Antis-594 | 0.681 | 0.142 | 0.270 | 0.451 | 27.7 |
| Antis-595 | 0.535 | 0.124 | 0.228 | 0.470 | 33.0 |

All data in $\mu mol/gFW^{-1}$

The invention claimed is:

1. A method for increasing the total free amino acid content of a plant or transformed progeny thereof, comprising;
   transforming a plant with a plant transformation vector comprising an isolated polynucleotide encoding a plastidial ATP/ADP translocator,
   determining the free amino acid content of the transformed plant compared to an untransformed control plant and selecting for an increase in the free amino acid content;
   wherein the total free amino acid content is increased compared to a untransformed control plant.

2. The method of claim 1 wherein the vector comprises the nucleotide sequence of SEQ ID NO: 1.

3. The method of claim 1 wherein the vector comprises the nucleotide sequence of SEQ ID NO: 2.

4. The method of claim 1 wherein the transformed plant or progeny thereof is potato or maize.

5. The method of claim 1, wherein the amino acids are one or more essential amino acids.

6. The method of claim 1 wherein the vector further comprises one or more operably linked regulatory nucleotide sequences.

7. The method of claim 6, wherein the one or more regulatory nucleotide sequences are selected from the group consisting of promoters, terminators, translation enhancers, nucleotide sequences for replication in a suitable host cell, nucleotide sequences for integration into a genome, and combinations thereof.

8. The method of claim 1 wherein the transformed plant or progeny thereof is used directly as a fodder plant.

* * * * *